US008485976B2

(12) United States Patent
Iimura et al.

(10) Patent No.: US 8,485,976 B2
(45) Date of Patent: Jul. 16, 2013

(54) ULTRASONIC DIAGNOSTIC APPARATUS

(75) Inventors: Takashi Iimura, Tokyo (JP); Koji Waki, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 0 days.

(21) Appl. No.: 13/061,226

(22) PCT Filed: Aug. 20, 2009

(86) PCT No.: PCT/JP2009/064538
§ 371 (c)(1),
(2), (4) Date: Feb. 28, 2011

(87) PCT Pub. No.: WO2010/024168
PCT Pub. Date: Mar. 4, 2010

(65) Prior Publication Data
US 2011/0152687 A1     Jun. 23, 2011

(30) Foreign Application Priority Data
Aug. 29, 2008   (JP) .................................. 2008-222613

(51) Int. Cl.
*A61B 8/14*   (2006.01)
(52) U.S. Cl.
USPC ............................ 600/443; 600/437; 600/440
(58) Field of Classification Search
USPC ................................................. 600/437–443
See application file for complete search history.

(56) References Cited

U.S. PATENT DOCUMENTS

| 2006/0173309 A1* | 8/2006 | Suzuki et al. .................. 600/437 |
| 2007/0032726 A1* | 2/2007 | Osaka et al. ................... 600/459 |
| 2008/0051659 A1* | 2/2008 | Waki et al. ..................... 600/443 |

(Continued)

FOREIGN PATENT DOCUMENTS

| EP | 1 637 082 A2 | 3/2006 |
| EP | 1 800 603 A1 | 6/2007 |

(Continued)

OTHER PUBLICATIONS

Supplementary European Search Report dated Dec. 6, 2012 for Application No. EP 09 80 9820.

*Primary Examiner* — Sanjay Cattungal
*Assistant Examiner* — Farshad Negarestan
(74) *Attorney, Agent, or Firm* — Antonelli, Terry, Stout & Kraus, LLP.

(57) ABSTRACT

Even when a region of interest (ROI) is changed on a frozen image, an elasticity image of ROI after the change can be displayed without executing re-measurement. An ultrasonic diagnostic apparatus 1 has a control unit 110 having a first ROI setting unit 38 and a second ROI setting unit 39. When ROI is set by the first ROI setting unit 38 of the control unit 110, an elasticity information calculating unit 32 sets an area larger than ROI as a calculation area, calculates distortion, elasticity modulus, etc. of a tissue corresponding to each measurement point on a tomographic image of the calculation area, generates elasticity information based on the distortion, the elasticity modulus, etc., and outputs the elasticity information to an elasticity information storing unit 33. The control unit 110 changes the position/size of ROI by the second ROI setting unit 39 under a state that the frozen image is displayed. The elasticity image constructing unit 34 reads the elasticity information corresponding to the changed ROI from the elasticity information storing unit 33, forms an elasticity image of the changed ROI and displays it on an image display unit 26.

9 Claims, 12 Drawing Sheets

U.S. PATENT DOCUMENTS

| | | | |
|---|---|---|---|
| 2008/0081993 A1* | 4/2008 | Waki | 600/438 |
| 2009/0124903 A1 | 5/2009 | Osaka | |
| 2009/0143675 A1 | 6/2009 | Suzuki et al. | |

FOREIGN PATENT DOCUMENTS

| | | |
|---|---|---|
| EP | 2 030 573 A1 | 3/2009 |
| JP | 2002304399 | 10/2002 |
| JP | 2005027941 | 2/2005 |
| JP | 2006122295 | 5/2006 |
| JP | 2007167291 | 7/2007 |
| WO | WO2006/054635 | 5/2006 |
| WO | WO2007/034738 | 3/2007 |
| WO | WO 2007/142255 A1 | 12/2007 |

* cited by examiner

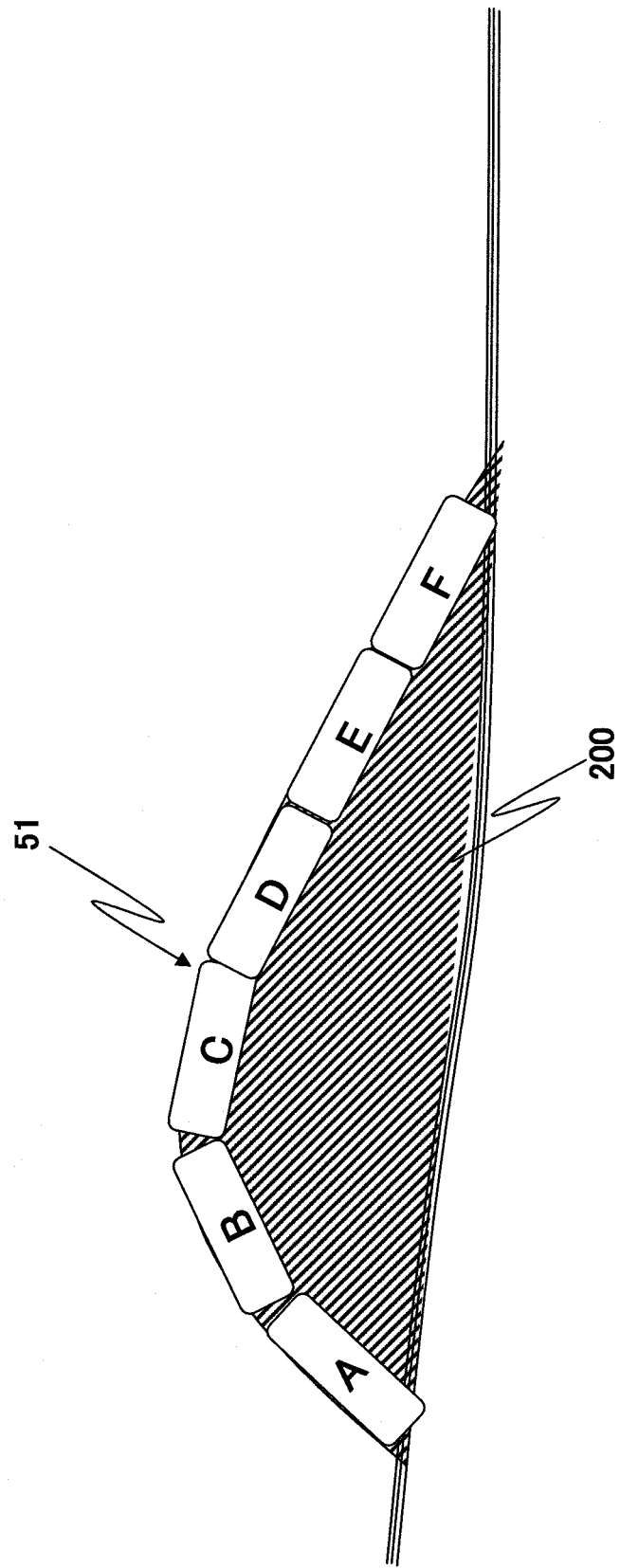

ULTRASONIC DIAGNOSTIC APPARATUS

TECHNICAL FIELD

The present invention relates to an ultrasonic diagnostic apparatus, and relates to an ultrasonic diagnostic apparatus having a function of displaying a tomographic image of an imaging target site in an examinee and an elasticity image representing hardness or softness of a living tissue.

BACKGROUND ART

The ultrasonic diagnostic apparatus transmits an ultrasonic wave to the inside of an examinee by an ultrasonic probe, receives an ultrasonic-wave reflection echo signal corresponding to acoustic impedance of each part of a tissue from the inside of the examinee to construct a tomographic image such as an ultrasonic tomographic image, and displays the tomographic image for diagnosis.

Furthermore, according to the ultrasonic diagnostic apparatus, an ultrasonic reception signal is measured while an examinee is pressed by an ultrasonic probe according to a manual or mechanical method, a displacement of each part of a living body caused by the press is determined on the basis of frame data of two ultrasonic reception signals which are different in measurement time, and an elasticity image representing hardness or softness of a living tissue is generated and displayed on the basis of the displacement data (for example, Patent Document 1).

Furthermore, elasticity information concerning a region of interest set by an operator is calculated, an elasticity image is generated on the basis of the elasticity information, and a tomographic image and an elasticity image are displayed (for example, Patent Document 2).

When a particularly detailed diagnosis is required, for example, a composite image comprising a tomographic image and an elasticity image is frozen, and a region of interest such as an affected region is observed on the basis of the frozen composite image.

PRIOR ART DOCUMENT

Patent Document

Patent Document 1: JP-A-2002-304399
Patent Document 2: JP-A-2007-167291

SUMMARY OF THE INVENTION

Problem to be solved by the Invention

For example, when an affected region or the like is observed on the basis of a frozen composite image, there is a case where it is required to be observed comparatively with elasticity information of a site of a tissue out of a set region of interest. In this case, it may be considered to move the region of interest on the frozen composite image or change the region of interest by changing the size so as to contain a site to be comparatively observed.

However, according to the prior arts such as the Patent Document 1, the elasticity information concerning only the region of interest before the change is required, and thus an elasticity image of the region of interest after the change cannot be constructed by merely changing the region of interest.

The problem to be solved by the invention resides in the fact that an elasticity image of a newly set region of interest can be displayed without re-measurement even when the region of interest is changed on a frozen composite image.

Means of Solving the Problem

The invention is based on an ultrasonic diagnostic apparatus having a tomographic image constructing unit that constructs a tomographic image on the basis of a reflection echo signal received by an ultrasonic probe for transmitting/receiving ultrasonic waves to/from an examinee; an elasticity information calculating unit that calculates elasticity information at a tomographic site of the examinee on the basis of the reflection echo signal; an elasticity image constructing unit that constructs an elasticity image on the basis of the elasticity information; an image composite unit that generates a composite image comprising the tomographic image and the elasticity image; and an image display unit that displays the composite image.

Particularly, in order to solve the problem, a freeze control unit configured to the composite image and region-of-interest setting unit that sets a region of interest on the frozen composite image are provided, and the elasticity image constructing unit constructs the elasticity image on the basis of the elasticity information of the region of interest set by the region of interest setting unit.

As described above, for example, when a composite image to be observed in detail is displayed during real-time measurement, the composite image is frozen, and when the region of interest on the frozen composite image is changed, an elasticity image of the region of interest after the change is constructed on the basis of the elasticity information of the region of interest after the change by the elasticity image constructing unit, and the composite image is constructed and displayed.

Here, the composite image contains composite images such as a composite image in which a tomographic image and an elasticity image are displayed to be arranged side by side, and a composite image in which both the tomographic image and the elasticity image are displayed to be superimposed on each other. Accordingly, even when a region of interest is changed on a frozen composite image, an elasticity image of a newly set region of interest can be displayed without re-measurement, and thus usability can be enhanced.

Furthermore, there may be provided an elasticity information storing unit that calculates and stores the elasticity information with respect to a calculation area of the region of interest set by the region-of-interest setting unit.

Here, the elasticity information calculating unit may calculate elasticity information with respect to a calculation area larger than the region of interest, and store the elasticity information into the elasticity information storing unit. Furthermore, the calculation area larger that the region of interest may be enlarged and set till a field of vision of a tomographic image or the like at maximum. However, it is preferable to set the size of the calculation area in accordance with an affected region or an observation site. Furthermore, the region-of-interest setting unit can set the position and/or size of the region of interest.

In this case, tomographic image storing unit that stores plural composite images time-sequentially is provided, and the elasticity information storing unit time-sequentially stores the elasticity information corresponding to the plural composite images, the freeze control unit displays a tomographic image read out from the composite image storing unit on the image display unit, and freezes the displayed composite image. Accordingly, a tomographic image, a composite image and elasticity information are time-sequentially stored in a cine memory, a frame memory or the like by executing a predetermined measurement. After the measurement, the tomographic image or the composite image in the cine memory or the like is reproduced, a composite image to be observed in detail is frozen and a region of interest is set on the frozen composite image, whereby elasticity images of plural sites to be comparatively observed are displayed without re-measurement. Therefore, usability can be enhanced.

Furthermore, the region-of-interest setting unit can set plural regions of interest on the frozen composite image. In this case, the elasticity image constructing unit can read out the elasticity information of the plural regions of interest from the elasticity information storing unit, construct the elasticity images of the plural regions of interest and output them to the image combining unit.

Furthermore, when plural regions of interest are set on a frozen composite image, the elasticity image constructing unit has normalization calculating unit that reads out, from the elasticity information storing unit, distortion information out of the elasticity information of the plural regions of interest set by the region-of-interest setting unit, calculates an average value of the distortion information over all the plural regions of interest, and normalizes the distortion information of the plural regions of interest with the calculated average value set as a reference value, and the elasticity image constructing unit can construct elasticity images of the plural regions of interest on the basis of the distortion information calculated by the normalization calculating unit, and output the elasticity images to the image combining unit. Normally, the distortion information is relative information of each region of interest, and thus the distortion information of different regions of interest cannot be compared with one another with no modification. In this point, the distortion information of the plural regions of interest are normalized with the average value set as a reference value, whereby the distortion information of the different regions of interest can be relatively grasped, and thus they can be compared with one another.

Furthermore, when plural regions of interest are set on a frozen composite image, there my be provided measurement area setting unit that sets a measurement area on each of the plural region of interest, and measurement area calculating unit that calculates the ratio of the elasticity information among the measurement areas, and displays the calculated ratio on the image displaying unit. Accordingly, it is difficult to compare the elasticity information of a site of interest on the basis of the difference in hue, brightness or the like of elasticity images of plural regions of interest which are set to be far away from one another, however, they can be easily compared with one another by displaying the ratio of the elasticity information.

Effect of the Invention

According to the invention, there is an effect that even when the region of interest is changed on the frozen composite image, an elasticity image of a newly set region of interest can be displayed without re-measurement.

BRIEF DESCRIPTION OF THE DRAWINGS

FIG. 12 is a diagram showing another embodiment of the ROI setting unit according to the third embodiment.

BEST MODES FOR CARRYING OUT THE INVENTION

Embodiments of an ultrasonic diagnostic apparatus to which the invention is applied will be described.

First Embodiment

Figure 1:
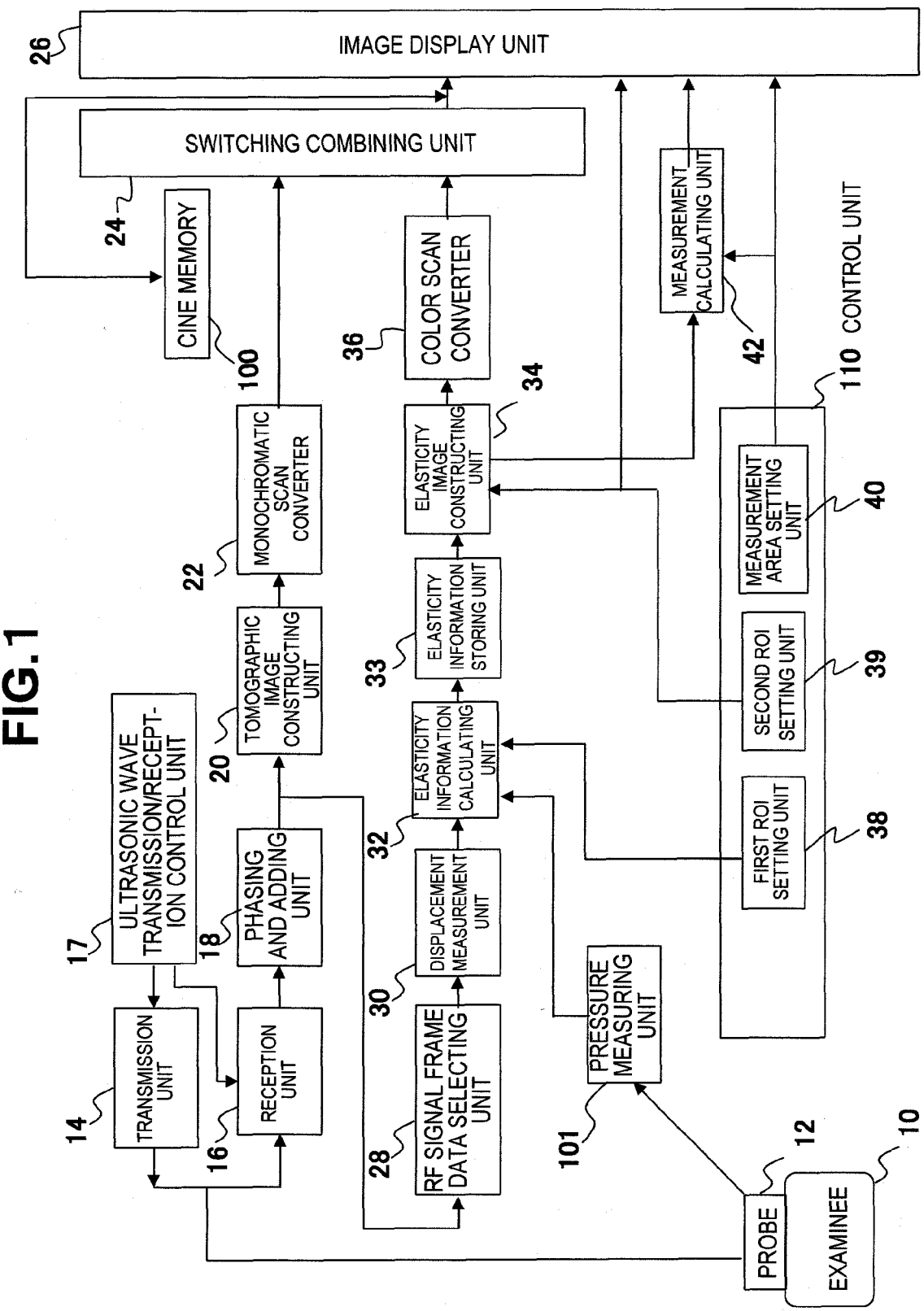
FIG. 1 is a block diagram showing the construction of an ultrasonic diagnostic apparatus according to a first embodiment to which the invention is applied.
Figure 2:
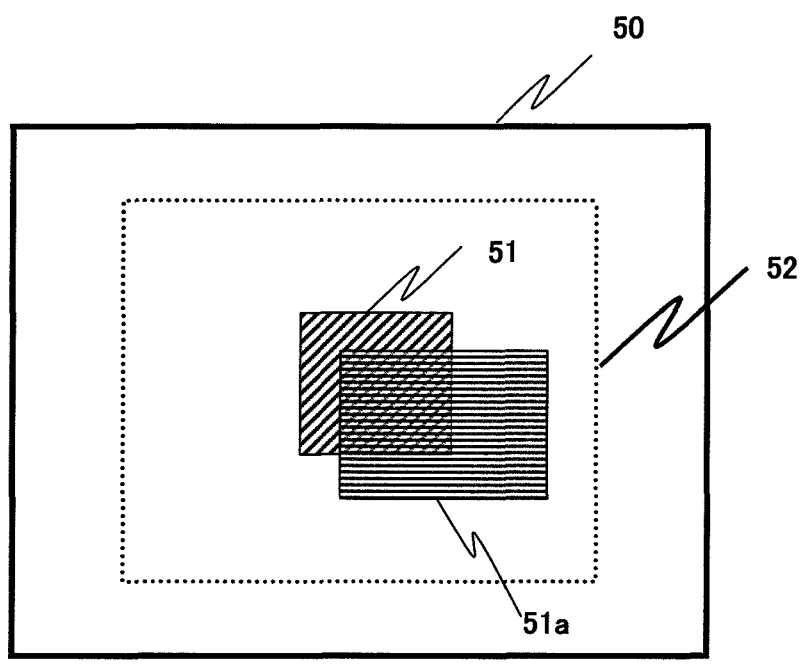
FIG. 2 is a diagram showing an operation area calculated by an elasticity information calculating unit shown in FIG. 1.
Figure 3:
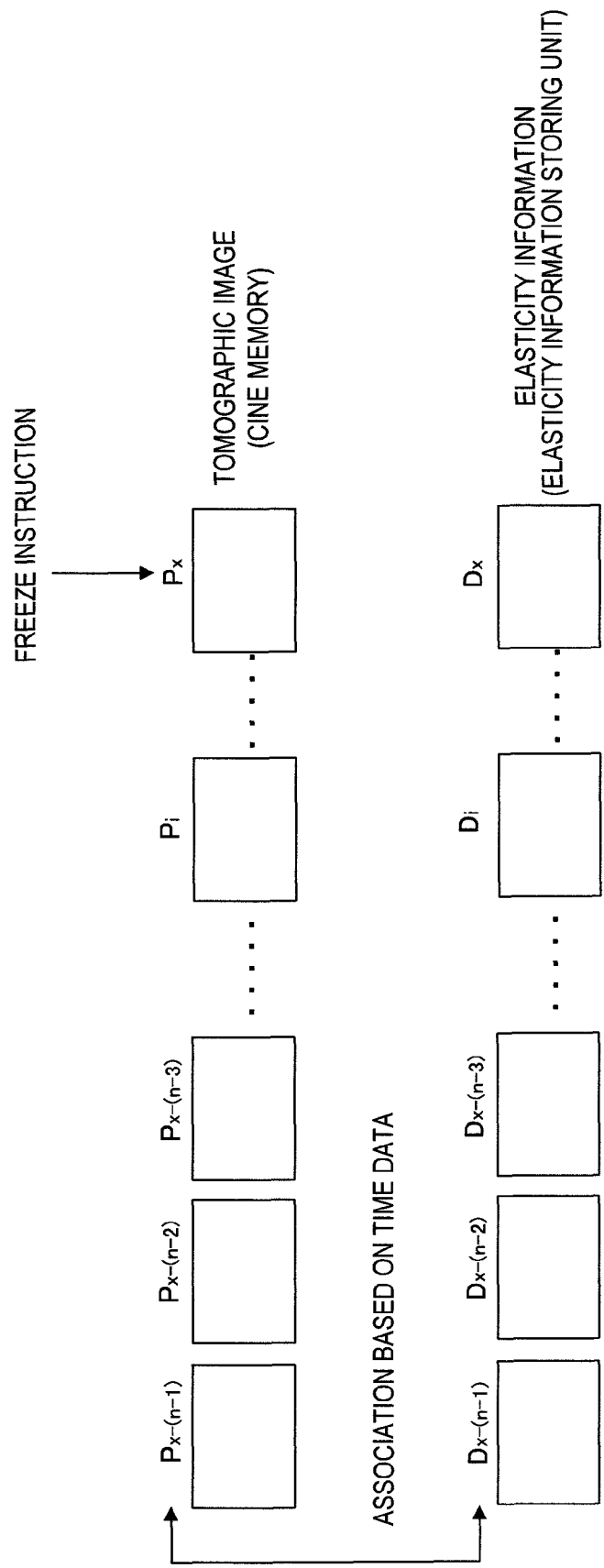
FIG. 3 is a diagram showing the relationship between frame data of a tomographic image stored in a cine memory and frame data of elasticity information stored in an elasticity information storing unit.
Figure 4:
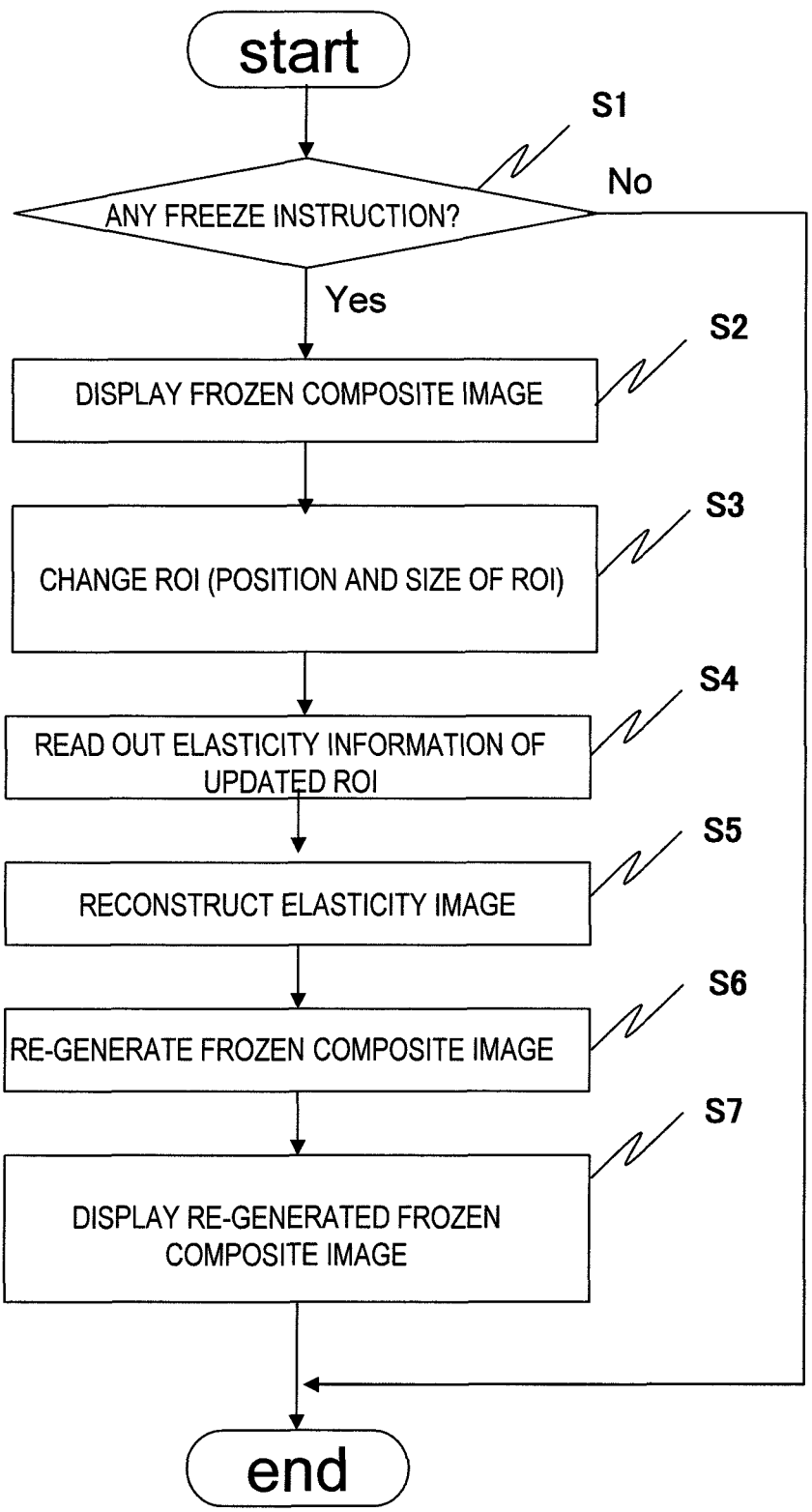
FIG. 4 is a flowchart showing the flow of processing of changing a region of interest when the ultrasonic diagnostic apparatus of FIG. 1 is frozen.
Figure 5:
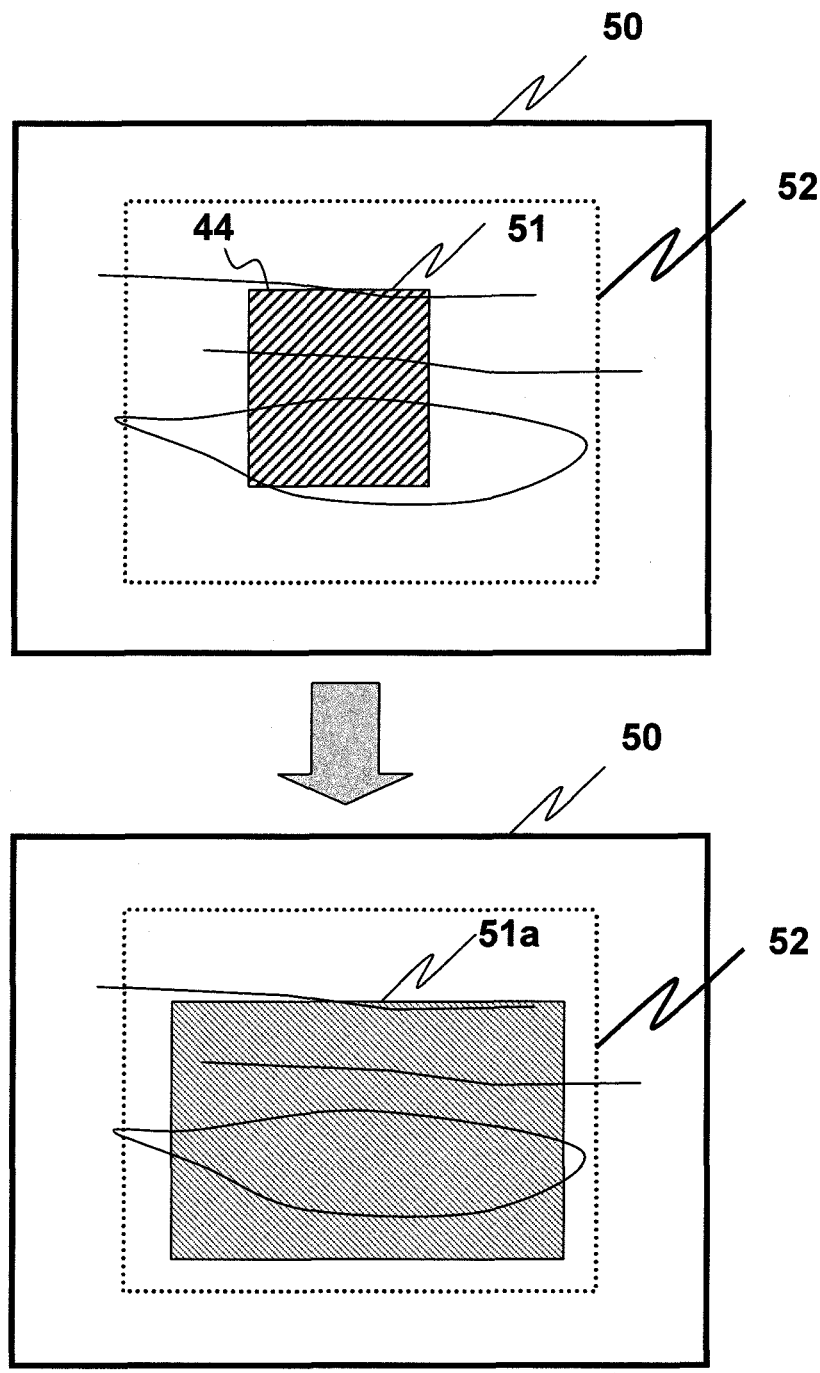
FIG. 5 is a diagram showing a state that the region of interest in the processing of FIG. 4 is changed.
Figure 6:
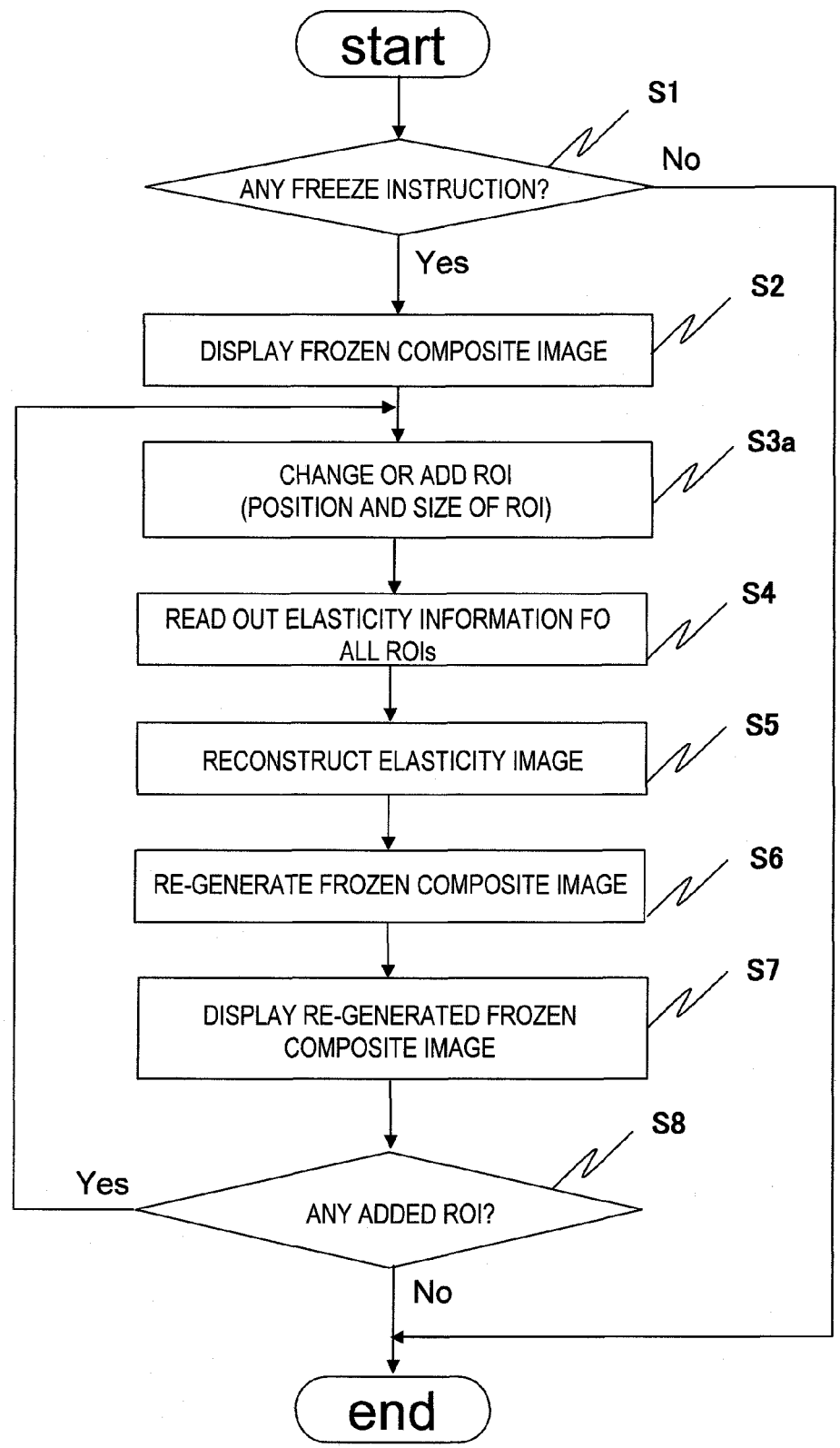
FIG. 6 is a flowchart showing a modification of the flow of the processing of changing the region of interest when the ultrasonic diagnostic apparatus of FIG. 1 is frozen.
Figure 7:
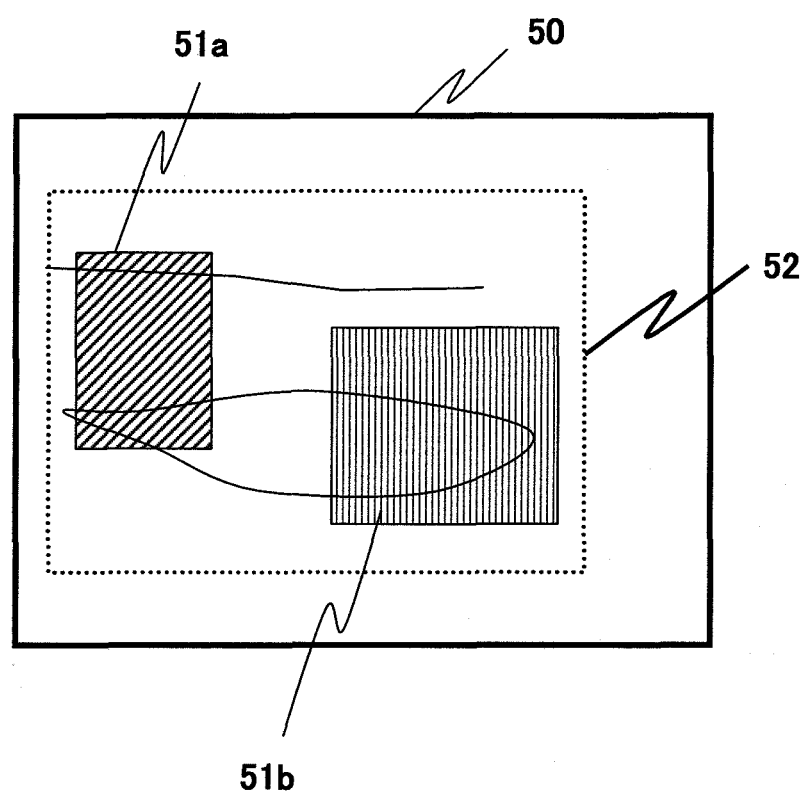
FIG. 7 is a diagram showing a state that the region of interest in the processing of FIG. 6 is changed.
Figure 8:
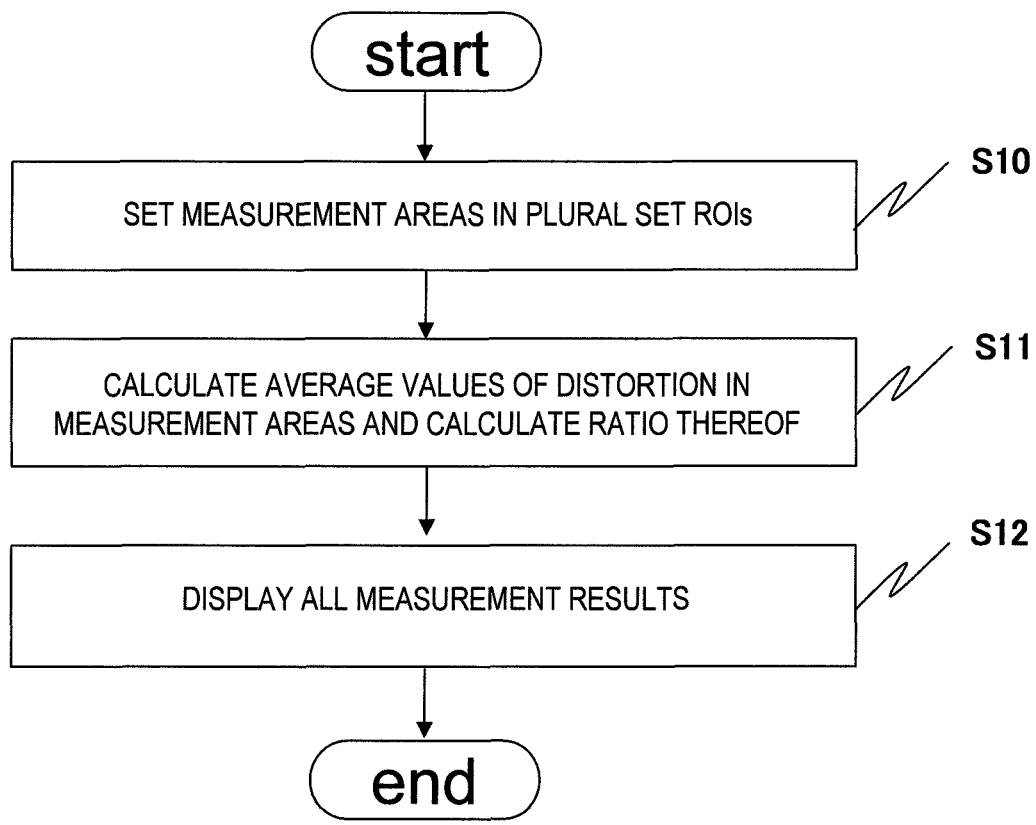
FIG. 8 is a flowchart showing the flow of processing of changing a region of interest when an ultrasonic diagnostic apparatus according to a second embodiment to which the invention is applied is frozen.
Figure 9:
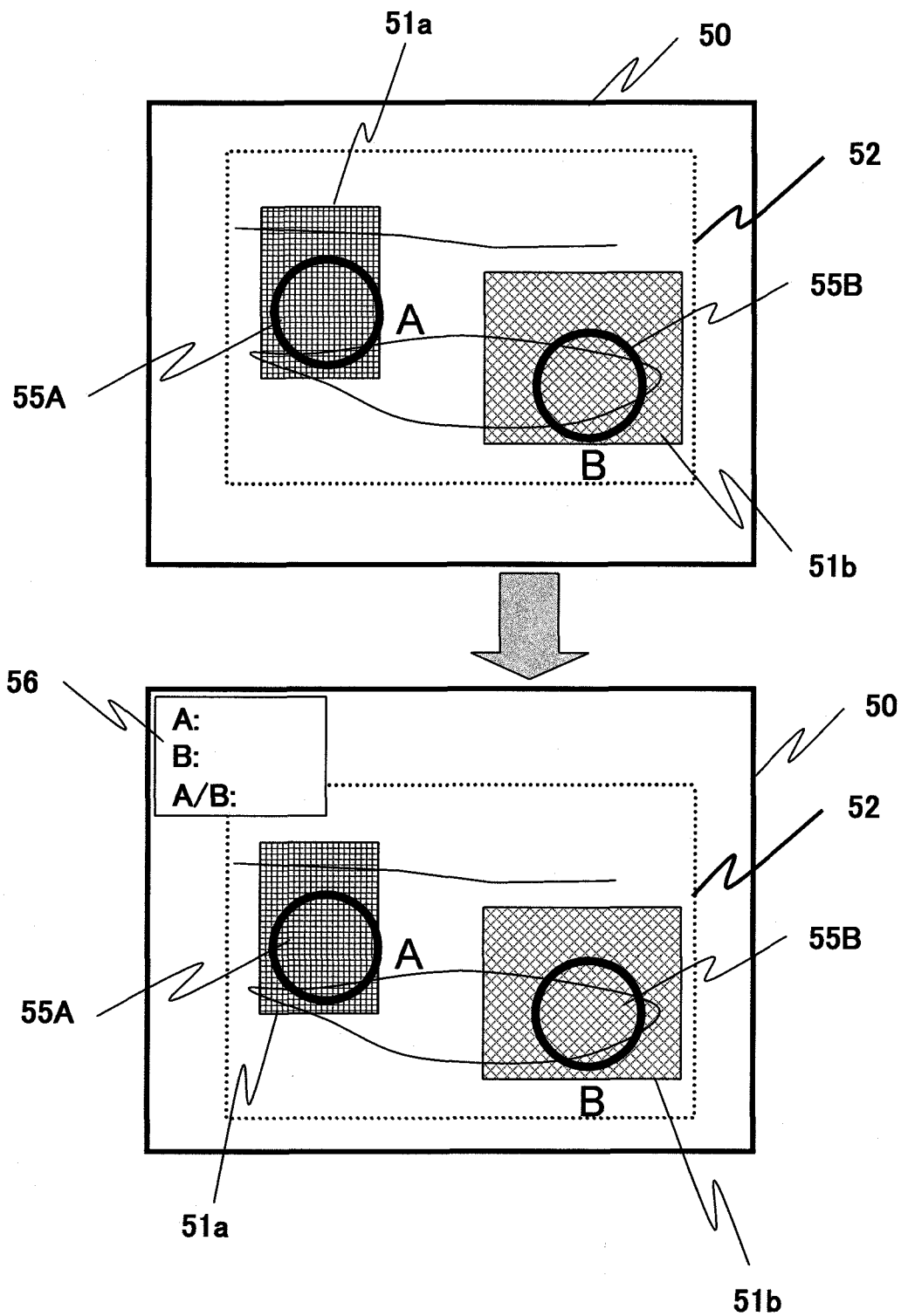
FIG. 9 is a diagram showing a state that the region of interest in the processing of FIG. 8 is changed.

A first embodiment of an ultrasonic diagnostic apparatus to which the invention is applied will be described with reference to FIGS. 1 to 9. FIG. 1 is a block diagram showing the construction of an ultrasonic diagnostic apparatus according to this embodiment, FIG. 2 is a diagram showing a calculation area which is calculated in an elasticity information calculating unit of this embodiment, FIG. 3 is a diagram showing the relationship between frame data of a tomographic image stored in a cine memory of this embodiment, and frame data of elasticity information stored in an elasticity information storing unit, FIG. 4 is a flowchart showing the flow of processing of changing the region of interest which is executed while a composite image in this embodiment is frozen, FIG. 5 is a diagram showing a state that the region of interest in the processing of FIG. 4 is changed, FIG. 6 is a flowchart showing a modification 1 of the flow of processing of changing the region of interest when this embodiment is frozen, FIG. 7 is a diagram showing a state that the region of interest in the processing of FIG. 6 is changed, FIG. 8 is a flowchart showing a modification 2 of the flow of processing of changing the region of interest under freezing in this embodiment of FIG. 1, and FIG. 9 is a diagram showing a state that the region of interest in the processing of FIG. 8 is changed.

As shown in FIG. 1, the ultrasonic diagnostic apparatus 1 has an ultrasonic probe 12 which is used in contact with an examinee 10, a transmission unit 14 for repetitively transmitting ultrasonic waves to the examinee 10 through the ultrasonic probe 12 at a time interval, a reception unit 16 for receiving a time-series reflection echo signal occurring from the examinee 10, an ultrasonic wave transmission/reception control unit 17 for controlling the transmission unit 14 and the reception unit 16, and a phasing and adding unit 18 for phasing and adding the reflection echo received by the reception unit 16.

The ultrasonic probe 12 is formed by arranging plural transducers, and has a function of transmitting/receiving ultrasonic waves by, the transducers to the examinee 10. The transmission unit 14 has a function of generating a wave transmission pulse for driving the ultrasonic probe 12 and generating ultrasonic waves, and setting a convergence point of the ultrasonic waves to be transmitted to some depth. The reception unit 16 amplifies a reflection echo signal received by the ultrasonic probe 12 with a predetermined gain to generate an RF signal, that is, a wave reception signal. The phasing and adding unit 18 receives the RF signal amplified by the reception unit 16 to perform phase control, and forms ultrasonic wave reception beams for one point or plural convergence points to generate RF signal frame data.

Furthermore, the ultrasonic diagnostic apparatus 1 is provided with a tomographic image constructing unit 20 as tomographic image constructing unit for constructing a shading tomographic image of an examinee, for example, (monochromatic) tomographic image of an examinee on the basis of RF signal frame data in which the RF signal phased and added in the phasing and adding unit 18 is set as frame data, a monochromatic scan converter 22 for converting an output signal of the tomographic image constructing unit 20 so that the output signal is matched with display of an image display unit 26 as image display unit, and a switching combining unit 24 as image combining unit for changing the combination rate of a tomographic image and an elasticity image (described later) and generating a composite image.

The tomographic image constructing unit 20 receives RF signal frame data from the phasing and adding unit 18 to perform signal processing such as gain correction, log compression, wave detection, edge enhancement, or filter processing to obtain tomographic image data. A monochromatic tomographic image output from the monochromatic scan converter 22 is input to the switching combining unit 24.

Furthermore, the ultrasonic diagnostic apparatus 1 is provided with an RF frame data selecting unit 28 for storing RF signal frame data output from the phasing and adding unit 18, and selecting two frame data different in measurement time, a displacement measuring unit 30 for measuring the displacement of a tissue of the examinee 10, an elasticity information calculating unit 32 as elasticity information calculating means for acquiring elasticity frame data as distortion, elasticity information such as elasticity modulus, or viscosity from displacement information measured by the displacement measuring unit 30, elasticity information storing unit 33 as elasticity information storing means for storing elasticity information calculated in the elasticity information calculating unit 32, an elasticity image constructing unit 34 as elasticity image constructing means for constructing a color elasticity image (hereinafter merely referred to as elasticity image) from the elasticity information storing unit 33, and a color scan converter 36 for converting an output signal of the elasticity image constructing unit 34 so that the output signal is matched with a display style of the image display unit 26.

When the elasticity information calculating unit 32 acquires an elasticity modulus, stress data at each measurement point is required. Therefore, in order to acquire the elasticity modulus, the ultrasonic diagnostic apparatus 1 is provided with a pressure measuring unit 101, and the elasticity information calculating unit 32 calculates the stress at a measurement point in the examinee 10 on the basis of the detection signal of a pressure sensor (not shown) provided around the ultrasonic wave transmission/reception face of the probe 12 detected by the pressure measuring unit 101.

Furthermore, the ultrasonic diagnostic apparatus 1 can superimpose a monochromatic tomographic image and a color elasticity image on each other or display them side by side with the switching combining unit 24 and the image display unit 26. Furthermore, a cine memory 100 constitutes the image storing unit, and the tomographic image and/or the elasticity image combined in the switching combining unit 24 is stored as image frame data in the cine memory 100. The cine memory 100 is configured so that selected image data can be transmitted to a recording medium (not shown) such as MO.

The RF signal frame data selecting unit 28 stores plural RF signal frame data from the phasing and adding unit 18, and selects one pair, that is, two RF signal frame data different in measurement time from the stored RF signal frame data group. For example, the RF signal frame data selecting unit 28 successively stores the RF signal frame data generated time-sequentially, that is, on the basis of the frame rate of images from the phasing and adding unit 18 into the RF frame data selecting unit 28, and selects stored RF signal frame data (N) as first data. Simultaneously, the RF signal frame data selecting unit 28 selects one RF signal frame data (X) from the RF signal frame data group (N−1, N−2, N−3, . . . , N−M) which were stored past in time. Here, N, M, X represent index numbers appended to the RF signal frame data, and are natural numbers.

The displacement measuring unit 30 executes one-dimensional or two-dimensional correlation processing from the selected pair of data, that is, the RF signal frame data (N) and the RF signal frame data (X) to acquire a displacement and a moving vector of the tissue corresponding to each point of a tomographic image, that is, a one-dimensional or two-dimensional displacement distribution concerning the direction and magnitude of the displacement. Here, the moving vector is detected by using a well-known method such as a block matching method, or a correlation method. For example, the block matching method executes the processing of dividing an image into blocks of N×N pixels, noting a block in a region of interest, searching, from a previous frame, a block which is most approximate to the block being noted, and refers to this block to determine a sample value on the basis of prediction coding, that is, difference.

The elasticity information calculating unit 32 determines the distortion at each measurement point of a calculation area larger than the set region of interest on the basis of a measurement value output from the displacement measuring unit 30, for example, a moving vector to generate distortion frame data, and stores the distortion frame data into the elasticity information storing unit 33. Furthermore, the elasticity information calculating unit 32 calculates an elasticity modulus of the tissue at each measurement point of the calculation area on the basis of the distortion and the pressure (stress) of each measurement point output from the pressure measuring unit 101, generates elasticity modulus frame data and stores the elasticity modulus frame data into the elasticity information storing unit 33.

At this time, the distortion is calculated by spatially differentiating the movement amount of the tissue, for example, the displacement. The elasticity modulus is calculated by dividing the pressure variation by the distortion variation. For example, when the displacement measured by the displacement measuring unit 30 is represented by L(X) and the pressure measured by the pressure measuring unit 101 is represented by P (X), the distortion value ΔS(X) can be calculated by spatially differentiating L(X), and thus it can be determined by using an arithmetic expression of $\Delta S(X)=\Delta L(X)/\Delta X$. Furthermore, the Young's modulus Ym(X) as an example of the elasticity modulus is calculated by the arithmetic expression of $Ym=(\Delta P(X)/\Delta S(X)$. The elasticity modulus of the tissue corresponding to each point of a tomographic image is determined from the Young's modulus Ym, and thus two-dimensional elasticity information can be continuously obtained. The Young's modulus is the ratio of a simple tensile stress applied to an object to distortion occurring in parallel to the tensile.

The elasticity information storing unit 33 stores elasticity frame data such as the distortion, or the elasticity modulus, calculated by the elasticity information calculating unit 32. The elasticity information is information representing the hardness or softness of the tissue, and contains physical quantities such as a displacement amount, a distortion amount, or an elasticity modulus, coefficients correlated with these physical quantities, etc.

The elasticity image constructing unit 34 is configured to contain a frame memory and an image processor, and it secure elasticity information output time-sequentially from the elasticity information calculating unit 32 into the frame memory, and executes image processing on the secured elasticity information.

The color scan converter 36 has a function of appending hue information to the elasticity information from the elasticity image constructing unit 34. That is, it performs the conversion to three primary colors of light, that is, red (R), green (G) and blue (B) on the basis of the elasticity information, for example.

For example, the distortion at each measurement point is normalized with the average value of the distortion of the whole region of interest set as a reference value, the hue of a measurement point having a large distortion is converted to a red-color code, and also the hue of a measurement point having a small distortion is converted to a blue-color code to thereby represent a distortion distribution. A monochromatic scan converter may be used in place of the color scan converter 36. In this case, an area whose distortion is measured to be large is set to be high in brightness, and conversely an area whose distortion is measured to be small is set to be low in brightness, whereby the distortion distribution can be represented.

The switching combining unit 24 has a frame memory, an image processor and an image selecting unit. Here, the frame memory stores tomographic image data from the monochromatic scan converter 22 and elasticity image data from the color scan converter 36. Furthermore, the image processor combines the tomographic image data and the elasticity image data secured in the frame memory while changing the combination ratio therebetween, for example. The composite image contains composite images such as a composite image in which the tomographic image and the elasticity image are displayed side by side, and a composite image in which a tomographic image and an elasticity image are displayed in superposition with each other. The brightness information and the hue information of each pixel of the composite image are obtained by adding respective information of a monochromatic tomographic image and a color elasticity image in the combination ratio. Furthermore, the image selecting unit selects an image to be displayed on the image display unit 26 from the tomographic image data and the elasticity image data in the frame memory and the composite image data of the image processor.

The ultrasonic diagnostic apparatus 1 has a control unit 110 for controlling the respective parts in the device. The control unit 110 is configured to have a first ROI setting unit 38 as region-of-interest setting means for setting a region of interest (hereinafter referred to as ROI) as an area whose elasticity image is generated. Furthermore, the control unit 110 is configured to have the function of freeze control unit for controlling the read-out of the cine memory 100 or the frame memory of the switching combining unit 24 on the basis of an input instruction to freeze the composite image.

Next, the construction of the feature portion of this embodiment will be described. A first feature portion of the invention resides in the fact that a freeze control unit for freezing a composite image and a region-of-interest setting unit (second ROI setting unit 39) for setting a region of interest on the frozen composite image are provided, and the elasticity image constructing unit 34 constructs an elasticity image on the basis of elasticity information of a region of interest set by the region-of-interest setting unit (second ROI setting unit 39).

Furthermore, the second feature portion of the invention resides in the fact that a measurement area setting unit 40 provided to the control unit 110 and a measurement calculating unit 42 are provided in addition to the first feature. The second feature will be described in connection with a second embodiment described later.

The elasticity information calculating unit 32 and the elasticity information storing unit 33 according to the first feature have the foregoing constructions. Furthermore, the second ROI setting unit 39 serves as region-of-interest changing means for changing ROI which is set by the first ROI setting unit 38 and displayed on the frozen composite image displayed on the image display unit 26. The elasticity image constructing unit 34 takes in coordinate data of ROI changed by the second ROI setting unit 39, and reads out the elasticity information of the area corresponding to the coordinate data concerned from the elasticity information storing unit 33 to generate an elasticity image of ROI after the change. Accordingly, the composite image of the elasticity image of ROI after the change is displayed through the color scan converter 36 and the switching combining unit 24 onto the image display unit 26.

Furthermore, as shown in FIG. 2, when ROI 51 is set on a tomographic image 50 from the monochromatic scan converter 22 by the first ROI setting unit 38 of the control unit 110, the elasticity information calculating unit 32 sets a preset area larger than ROI 51 as a calculation area 52, calculates the distortion, the elasticity modulus, etc. corresponding to each measurement point on the tomographic image of the calculation area 52, generates elasticity information based on the distortion, the elasticity modulus, etc., that is, elasticity frame data, and outputs the elasticity frame data to the elasticity information storing unit 33.

The elasticity image constructing unit 34 constructs (generates) an elasticity image of the set ROI 51 on the basis of the elasticity information stored in the elasticity information storing unit 33, and outputs the generated elasticity image to the switching combining unit 24.

Furthermore, as shown in FIG. 3, the cine memory 100 successively stores the tomographic image data output from the monochromatic scan converter 22, and frame-basis tomographic image frame data (Px–(n–1), Px–(n–2), Px–(n–3), . . . , Pi, . . . Px) (here, n, i, x represent natural numbers). The elasticity information storing unit 33 stores elasticity information frame data (Dx–(n–1), Dx–(n–2), Dx–(n–3), . . . , Di, . . . , Dx) comprising elasticity information which is associated with the tomographic image frame data stored in the cine memory 100 on the basis of time data.

The elasticity information frame data (Dx–(n–1), Dx–(n–2), Dx–(n–3), . . . , Di, . . . , Dx) time-sequentially correspond to the tomographic image frame data (Px–(n–1), Px–(n–2), Px–(n–3), ..., Pi, ..., Px), however, when the elasticity information is not calculated between adjacent frames, but calculated every some frames, past elasticity information frame data which is just near in terms of time is treated as data corresponding to the tomographic image frame data. That is, the elasticity information is calculated by selecting two RF signal frame data different in measurement time from the RF signal frame data group which is stored in the past. Therefore, a pair of RF signal frame data used for the calculation are not necessarily limited to a pair of adjacent RF signal frame data.

When a freeze instruction for freezing a composite image is input from the control unit 110 through an input unit (not shown), the latest tomographic image Px and the elasticity image Dx which are output from the frame memory of the switching combining unit 24 to the image display unit 26 are freeze-displayed as a still image under real-time measurement. Not limited to the real-time measurement, the image frame data stored in the cine memory 100 may be reproduced and displayed on the image display unit 26 in accordance with an instruction input from the control unit 110.

As described with reference to FIG. 2, the elasticity information Dx is calculated for the calculation area 52 which is an area larger than ROI 51. According to this embodiment, with respect to the elasticity image constructing unit 34, for example, a composite image under real-time measurement is frozen. Then, changed ROI 51a corresponding to the freeze-displayed composite image is displayed on the frozen composite image on the basis of an instruction of changing ROI 51 (position or/and size) from the second ROI setting unit 39. The elasticity image constructing unit 34 constructs an elasticity image on the basis of the coordinate data of ROI 51a input from the second ROI setting unit 39 by using the elasticity information Dx in the calculation area 52 which is stored in the elasticity information storing unit 33, and outputs the elasticity image to the color scan converter 36, whereby the elasticity image of the changed ROI 51a is displayed on the image display unit 26.

When the composite image is frozen not under the real-time measurement, but by reproducing and displaying the image frame data stored in the cine memory 100, the elasticity information of the area corresponding to ROI 51a of the frozen composite image is read out from the elasticity storing unit 33, and the elasticity image on the image display unit 26 is changed.

Next, the flow of the processing of changing the position, size of ROI 51a in the second ROI setting unit 39 under the display state of the frozen composite image will be described with reference to FIG. 4. In this specific example, the control unit 110 changes the position, size of ROI 51a by the second ROI setting unit 39 under the display state of the frozen composite image. Specifically, the control unit 110 determines whether there is a freeze instruction from an input unit (not shown) (step S1). In a case where there is a freeze instruction, when the composite image stored in the cine memory 100 is reproduced and displayed on the image display unit 26, the control unit 110 freezes the composite image at the time when the freeze instruction is input (step S2). Subsequently, the position, size of ROI 51a on the frozen composite image are changed and displayed on the basis of the instruction input from the second ROI setting unit 39 to the image display unit 26 (step S3).

On the basis of the coordinate data of after-change ROI 51a input from the second ROI setting unit 39, the elasticity image constructing unit 34 reads out elasticity information at the position and/or the size after the change of ROI 51a in the calculation area 52 from the elasticity information storing unit 33 (step S4), and constructs an elasticity image in the after-change ROI 51a (step S5).

FIG. 5 shows variation of the display state from pre-change ROI 51 to after-change ROI 51a on the tomographic image 50 when the position and the size of ROI 51 are changed by the second ROI setting unit 39 under the display state of the frozen composite image. The elasticity image constructing unit 34 constructs an elasticity image corresponding to ROI 51a by using the elasticity information in the calculation area 52 which is stored in the elasticity information storing unit 33. The elasticity images constructed by the elasticity image constructing unit 34 are added and combined by the switching combining unit 24 and then displayed on the screen of the image display unit 26.

As described above, in this embodiment, a desired area can be set as a new region of interest by the change information of the position and/or size of ROI 51a under the state that the composite image under real-time measurement or the composite image when the image of the cine memory 100 is reproduced on a non-real-time basis is freeze-displayed. Accordingly, the elasticity image in the changed ROI 51a can be constructed, and detailed information concerning the hardness or softness of the tissue of the changed region of interest can be obtained.

Accordingly, according to this embodiment, the elasticity information is calculated for the calculation area 52 larger than the set ROI 51, and stored in the elasticity information storing unit 33. Therefore, when a composite image which is required to be observed in detail under real-time, measurement is displayed, the composite image is frozen. When the position and size of ROI 51a on the frozen composite image are changed, the elasticity information of ROI 51a after the change is read out from the elasticity information storing unit 33 by the elasticity image constructing unit 34, the elasticity image of after-change ROI 51a is constructed, and the composite image is constructed and displayed. Accordingly, even when ROI 51a is changed on the freeze image, the elasticity image of the after-change region of interest can be displayed without re-measurement. Therefore, a site to be comparatively observed can be compared on a still image in detail, and thus usability can be enhanced.

A freeze instruction is made at a suitable timing when a composite image to be observed in detail is displayed while composite images stored in the cine memory 100 are repetitively displayed as a moving image on the image display unit 26, whereby a suitable diagnosis can be performed.

MODIFICATION

Next, a modification of this embodiment will be described with reference to FIGS. 6 and 7. In this modification, ROI 51 is changed on the frozen composite image, new ROI 51a and ROI 51b are set, and distortion information of two ROI 51a and ROI 51b are normalized to be relatively comparable with each other.

That is, the second ROI setting unit 39 adds plural ROI 51a, ROI 51b, etc. on the frozen composite image, and also the positions and/or sizes of the plural ROI 51a and ROI 51b are changed/set. The flow of the processing is substantially identical to that shown in FIG. 4, and only the different point will be described.

In this modification, as shown in FIG. 6, the control unit 110 outputs the information concerning the position and/or size of ROI set by the second ROI setting unit 39 to the elasticity image constructing unit 34 to thereby instruct the change of ROI 51 (step S3a).

Furthermore, after the processing of the step S7, the control unit 110 determines whether there is any ROI to be further added (step S8). The control unit 110 returns to the step S3a when there is ROI to be added, and finishes the processing when there is no ROI to be added. Accordingly, as shown in FIG. 7, the control unit 110 sets (changes) plural ROI 51a and 51b. The other processing is identical to that of FIG. 4.

Through this processing, the elasticity image corresponding to each individual area is constructed in the elasticity image constructing unit 34. The constructed elasticity images are added and combined with one another by the switching and combining unit 24, and displayed on the screen of the image display unit 26.

In this modification 1, a normalization calculating unit is provided to the elasticity image constructing unit 34, and the normalization calculating unit reads out the distortion information out of the elasticity information of ROI 51a, 51b set by the second ROI setting unit 39 from the elasticity information storing unit 33. The average value of the distortion information of two ROIs 51a, 51b is calculated, and the distortion information of the two ROIs 51a, 51b is normalized with the calculated average value set as a reference value. The elasticity images of ROIs 51a, 51b are constructed on the basis of the distortion information of the two ROIs 51a, 51b calculated by the normalization calculating unit, and output to the image combining unit.

According to this embodiment, the distortion image represents relative elasticity of each measurement point in one ROI, and thus absolute elasticity cannot be recognized. However, distortion images obtained by normalizing distortions of two sites are compared with each other, whereby the elasticity of an affected region can be relatively recognized. For example, fat, etc. are constant distortion information having little difference among individuals. Therefore, one ROI is set in a fat layer, and the other ROI is set in an affected region, whereby distortion of the affected region can be estimated with remarkable accuracy. Furthermore, one ROI is set to an affected region and the other ROI is set to a different site of the affected region, whereby the difference in elasticity within the same affected region can be objectively estimated.

Furthermore, in the foregoing description, it is mainly described that the after-change ROI 51a is set to be larger than the original ROI 51. However, the invention is not limited to this embodiment, and the after-change ROI 51a may be set to be smaller than the original ROI 51 on the frozen composite image. Accordingly, a distortion distribution image in ROI is obtained, and thus a diagnosis can be performed by observing the hardness of the tissue in more detail.

Second Embodiment

A second embodiment of an ultrasonic diagnostic apparatus to which the invention is applied will be described with reference to FIGS. 8 and 9. This embodiment corresponds to a second feature portion of the invention as described above, and is characterized in that a measurement area setting unit 40 provided to the control unit 110 and a measurement area calculating unit 42 are provided in addition to the first embodiment.

The measurement area setting unit 40 sets a measurement area in each of plural ROIs displayed on a frozen composite image, and also outputs coordinate data of these measurement areas to the measurement calculating unit 42. The measurement calculating unit 42 reads out the elasticity information of the areas corresponding to the plural set measurement areas from the elasticity information storing unit 33, calculates the ratio of the elasticity information among the measurement areas on the basis of the elasticity information of the measurement areas, and outputs the calculation result concerned to the image display unit 26 to perform a numerical display.

That is, as shown in FIG. 8, after the processing of the step S7 of FIG. 4, the control unit 110 sets measurement areas 55A and 55B as shown in FIG. 9 on the plural ROIs 51a and 51b (step S10). The measurement calculating unit 44 calculates the distortion average values "A", "B" in the respective measurement areas 55A and 55B and the ratio "A/B" (step S11), and numerically displays the calculation result in a calculation display area 56 of the image display unit 26 (step S12).

That is, the ratio in hardness between non-adjacent tissues can be quantitatively estimated by a conventional method. However, it is required to set ROI at a larger size so as to specify a tissue, and thus unnecessary data may affect a quantitative estimation of the ratio. In this embodiment, in addition to the effect of the first embodiment, measurement areas to be particularly noted are respectively set on the non-adjacent plural ROIs in a pinpoint style, whereby elasticity information, for example, distortion is determined at these measurement areas with high precision without re-measurement, and the ratio of these elasticity information is further determined, whereby accurate diagnosis can be performed.

For example, when ROI 51b is set on a fat tissue and ROI 51a is set on a tissue being noted, the distortion value in the fat tissue is substantially constant because the distortion of the fat tissue has little difference among individuals. Therefore, the distortion "B" in the measurement area on ROI 51b (fat tissue) is set as a reference, and the ratio "A/B" of the distortion value "A" in the measurement area of ROI 51a (tissue being noted) to the distortion "B" is calculated and numerically displayed in the calculation display area 56, whereby information on hardness or softness of the tissue being noted can be numerically (quantitatively) obtained.

According to this embodiment, in addition to the effect of the first embodiment, the ratio of elasticity information is calculated among plural measurement areas set on plural ROIs, and the ratio is displayed on the image display unit 26, whereby the hardness can be determined with high precision among measurement areas of plural tissues, and the elasticity information thereof, for example, the ratio of the distortion can be displayed on the composite image, so that the elasticity of a site being noted can be quantitatively estimated.

Third Embodiment

Here, an example in which the first and second embodiments are applied for a specific ultrasonic diagnosis will be described with reference to FIGS. 10 to 12. This embodiment is an example suitable for a diagnosis relating to plaque occurring on a blood vessel wall of carotid artery.

Figure 10:
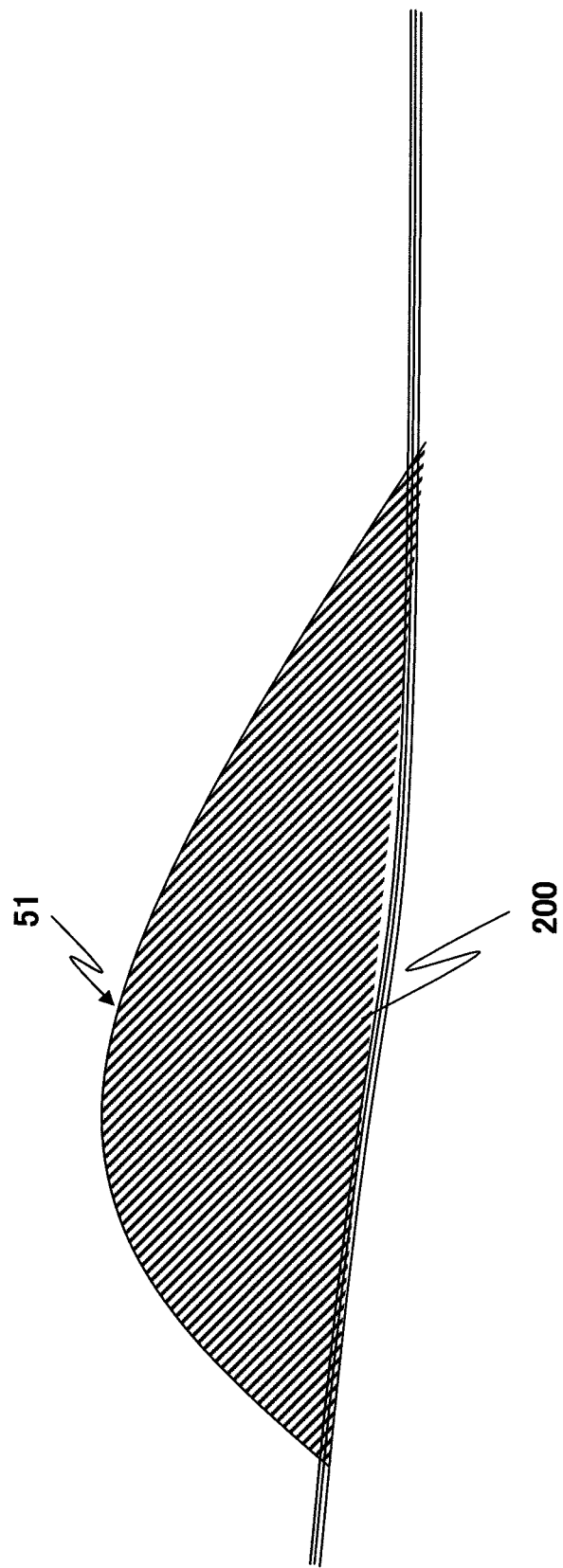
FIG. 10 is a diagram showing an example of an ROI setting unit of an ultrasonic diagnostic apparatus according to a third embodiment to which the invention is applied.

As shown in FIG. 10, the first ROI setting unit 38 manually or automatically sets ROI 51 in conformity with a given tissue (for example, plaque occurring on the blood vessel wall of carotid artery) 200. Specifically, the outer frame of plaque 200 may be specified by using the characteristic of the plaque 200. The characteristic of the plaque 200 resides in the fact that the plaque exists on the surface of the wall of carotid artery, there is no Doppler signal as a blood flow signal, etc.

In this case, a brightness distribution in the thickness direction of the wall of tomographic image data is obtained. A local maximum point having the maximum brightness of the brightness distribution is set as an outer membrane reference point, and a second local maximum point appearing at the inside (blood flow side) of the outer membrane reference point is set as an inner membrane reference point. A tissue having high brightness at the inside (blood flow side) of the inner membrane reference point is recognized. Furthermore, an area providing no Dropper signal out of the recognized high-brightness tissue is recognized as the plaque 200, and the outer frame of the plaque 200 is specified. The outer frame is set as the boundary of ROI 51.

Figure 11:
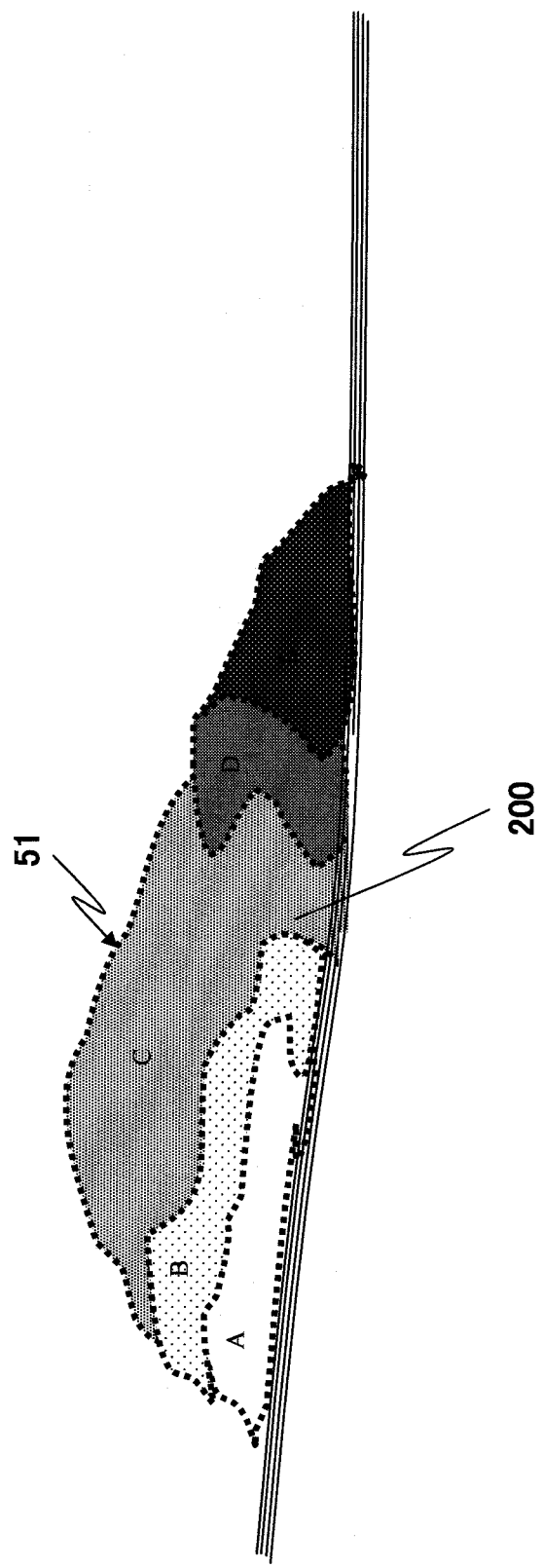
FIG. 11 is a diagram showing another example of the ROI setting unit according to the third embodiment.

Furthermore, as shown in FIG. 11, the first ROI setting unit 38 can set plural, for example, five ROI-A, ROI-B, ROI-C, ROI-D, ROI-E in the given predetermined tissue (for example, the plaque occurring on the blood vessel wall of the carotid artery) 200. As an example, it is assumed that ROI-A has brightness ranging from 1 to 30, ROI-B has brightness ranging from 31 to 60, ROI-C has brightness ranging from 61 to 90, ROI-D has brightness ranging from 91 to 120 and ROI-E has brightness ranging from 121 to 150. As described above, ROI-A to ROI-E can be automatically set on the basis of the brightness of the tomographic image data, and a detailed diagnosis can be performed on the basis of plural elasticity images in the plaque 200. In FIG. 11, "ROI-A" is abbreviated as "A", and "ROI-" is omitted.

Furthermore, as shown in FIG. 12, the first ROI setting unit 38 can set plural ROIs on the surface of the plaque 200. For example, an operator specifies the outer frame of the plaque of the tomographic image by using the first ROI setting unit 38. Accordingly, the first ROI setting unit 38 sets plural rectangular ROI-A to ROI-F along the specified outer frame of the plaque 200. For example, the boundary between a place providing no blood flow signal and a place providing a blood flow signal is analyzed as the surface of the plaque 200 by using the Doppler signal, and ROI-A to ROI-F are set to the boundary. Accordingly, no ROI is set between the plaque 200 providing no blood flow signal and the wall providing no blood flow signal. That is, ROI is set on only the surface of the plaque 200, and a detailed diagnosis based on plural elasticity images in the neighborhood of the surface of the plaque 200 can be performed. In FIG. 12, for example, "ROI-A" is abbreviated as "A", and "ROI-" is omitted.

DESCRIPTION OF REFERENCE NUMERALS

1 ultrasonic diagnostic apparatus, 10 examinee, 12 ultrasonic probe, 20 tomographic image constructing unit, 22 monochromatic scan converter, 24 switching combining unit, image display unit, 28 RF frame data selecting unit, 30 displacement measuring unit, 32 elasticity information calculating unit, 33 elasticity information storing unit, 34 elasticity image constructing unit, 36 color scan converter, first ROI setting unit, 39 second ROI setting unit, 40 measurement area setting unit, 42 measurement calculating unit, 100 cine memory, 101 pressure measuring unit, 110 control unit

The invention claimed is:

1. An ultrasonic diagnostic apparatus, comprising:
   a tomographic image constructing unit configured to construct a tomographic image on the basis of a reflection echo signal received by an ultrasonic probe configured to transmit ultrasonic waves to and receive ultrasonic waves from an examinee;
   an elasticity information calculating unit configured to calculate elasticity information at a tomographic site of the examinee on the basis of the reflection echo signal;
   an elasticity image constructing unit configured to construct an elasticity image on the basis of the elasticity information of a region-of-interest set by a first region-of-interest setting unit;
   an image combining unit configured to generate a composite image comprising the tomographic image and the elasticity image;
   an image display unit configured to display the composite image;
   a control unit configured to freeze the composite image; and
   a second region-of-interest setting unit configured to at least one of change the first region of interest and set a second region-of-interest on the frozen composite image;
   wherein when the first region-of-interest on the frozen composite image is changed by the second region-of-interest setting unit, the elasticity image constructing unit constructs an elasticity image of the changed first region-of-interest on the basis of stored elasticity information of a region including the first region-of-interest.

2. The ultrasonic diagnostic apparatus according to claim 1, further comprising:
   an elasticity information storing unit configured to calculate and store the elasticity information, with respect to the region including the first region-of-interest set by the first region-of-interest setting unit.

3. The ultrasonic diagnostic apparatus according to claim 1, further comprising:
   a composite image storing unit configured to time-sequentially store plural composite images;
   an elasticity information storing unit configured to time-sequentially store the elasticity information corresponding to the plural composite images; and
   wherein the control unit is configured to cause the image display unit to display a composite image read out from the composite image storing unit, and to freeze the displayed composite image.

4. The ultrasonic diagnostic apparatus according to claim 1,
   wherein the second region-of-interest setting unit is configured to set a plurality of second regions-of-interest on the frozen composite image;
   wherein the elasticity image constructing unit is configured to construct elasticity images of the plurality of second regions-of-interest based on the elasticity information of the plurality of second regions-of-interest-set by the second region-of-interest image setting unit, and to output the elasticity images to the image combining unit.

5. The ultrasonic diagnostic apparatus according to claim 1,
   wherein the second region-of-interest setting unit is configured to set a plurality of second regions-of-interest on the frozen composite image, and
   wherein the elasticity image constructing unit has a normalization calculating unit configured to determine an average value of distortion information of all the plurality of second regions-of-interest on the basis of distortion information out of the elasticity information of the plurality of second regions-of-interest set by the second region-of-interest setting unit, to construct elasticity images of the plurality of second regions-of-interest on the basis of the distortion information calculated by the normalization calculating unit, and to output the elasticity images to the image combining unit.

6. The ultrasonic diagnostic apparatus according to claim 1,
   wherein the second region-of-interest setting unit is configured to set a plurality of second regions-of-interest on the frozen composite image;
   wherein the control unit further includes a measurement area setting unit configured to set a measurement area on each of the plurality of second regions-of-interest; and wherein a measurement area calculating unit configured to calculate the ratio of the elasticity information among the measurement areas and displays the ratio on the image display unit.

7. The ultrasonic diagnostic apparatus according to claim 1, wherein the second region-of-interest setting unit is configured to change at least one of the position and the size of the first region-of-interest.

8. The ultrasonic diagnostic apparatus according to claim 1, wherein the composite image is a composite image in which the tomographic image and the elasticity image are displayed side by side, or a composite image in which the tomographic image and the elasticity image are displayed in superimposition with each other.

9. The ultrasonic diagnostic apparatus according to claim 1, wherein a distortion at each measurement point is normalized with an average value of the distortion of the region including the first region-of-interest set as a reference value, the hue of a measurement point having a large distortion is converted to a red-color code, and also the hue of a measurement point having a small distortion is converted to a blue-color code to thereby represent a distortion distribution.

* * * * *